United States Patent
Matsumoto

(10) Patent No.: US 12,363,823 B2
(45) Date of Patent: Jul. 15, 2025

(54) STRETCHABLE MOUNTING SUBSTRATE

(71) Applicant: Murata Manufacturing Co., Ltd., Nagaokakyo (JP)

(72) Inventor: Tadahiko Matsumoto, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 254 days.

(21) Appl. No.: 17/978,357

(22) Filed: Nov. 1, 2022

(65) Prior Publication Data

US 2023/0048568 A1 Feb. 16, 2023

Related U.S. Application Data

(63) Continuation of application No. PCT/JP2022/014498, filed on Mar. 25, 2022.

(30) Foreign Application Priority Data

Jun. 3, 2021 (JP) ................................. 2021-093823

(51) Int. Cl.
*H05K 1/02* (2006.01)
*A61B 5/25* (2021.01)
(Continued)

(52) U.S. Cl.
CPC ............. *H05K 1/0283* (2013.01); *A61B 5/25* (2021.01); *H05K 1/113* (2013.01); *H05K 1/118* (2013.01);
(Continued)

(58) Field of Classification Search
None
See application file for complete search history.

(56) References Cited

U.S. PATENT DOCUMENTS

2020/0258840 A1* 8/2020 Wakaki ................... H01L 23/12
2021/0212202 A1* 7/2021 Tomoda ............... H05K 1/0283
2022/0312587 A1* 9/2022 Nishida ............... H05K 1/0283

FOREIGN PATENT DOCUMENTS

JP H0750462 A 2/1995
JP 2004303944 A 10/2004
(Continued)

OTHER PUBLICATIONS

International Search Report in PCT/JP2022/014498, mailed May 31, 2022, 3 pages.

*Primary Examiner* — Krystal Robinson
(74) *Attorney, Agent, or Firm* — ArentFox Schiff LLP

(57) ABSTRACT

A stretchable mounting substrate that includes: a stretchable wiring substrate, the stretchable wiring substrate including a stretchable base material and a stretchable wiring arranged on the stretchable base material; and a module on a surface of the stretchable wiring substrate, the module including a multilayer substrate, a plurality of electronic components on a principal surface of the multilayer substrate, a plurality of first electrodes and a plurality of second electrodes, and internal wirings inside the multilayer substrate. The module has a first electrode arrangement region where the plurality of first electrodes are arranged and a second electrode arrangement region where the plurality of second electrodes are arranged, and includes a node electrode pair, and the internal wiring of the node electrode pair and the stretchable wiring on the stretchable base material intersect each other in plan view of the stretchable wiring substrate.

13 Claims, 4 Drawing Sheets

(51) Int. Cl.
*H05K 1/11* (2006.01)
*H05K 1/18* (2006.01)

(52) U.S. Cl.
CPC ....... *H05K 1/181* (2013.01); *H05K 2201/041* (2013.01); *H05K 2201/10522* (2013.01); *H05K 2201/10545* (2013.01)

(56) References Cited

FOREIGN PATENT DOCUMENTS

| | | | |
|---|---|---|---|
| JP | 2014162124 | A | 9/2014 |
| JP | 2017147379 | A | 8/2017 |
| JP | 2020174067 | A | 10/2020 |

\* cited by examiner

FIG. 1 - PRIOR ART
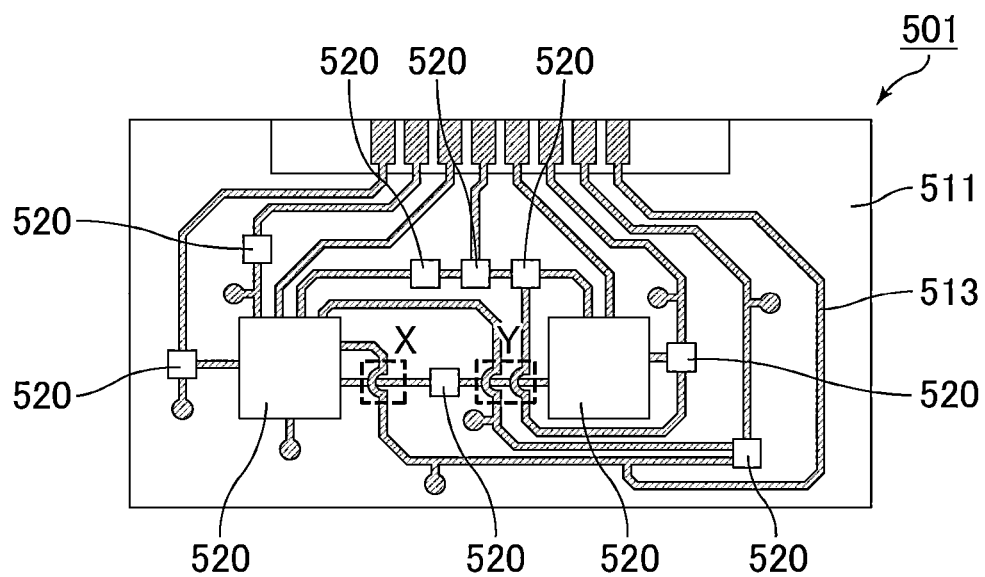
FIG. 2
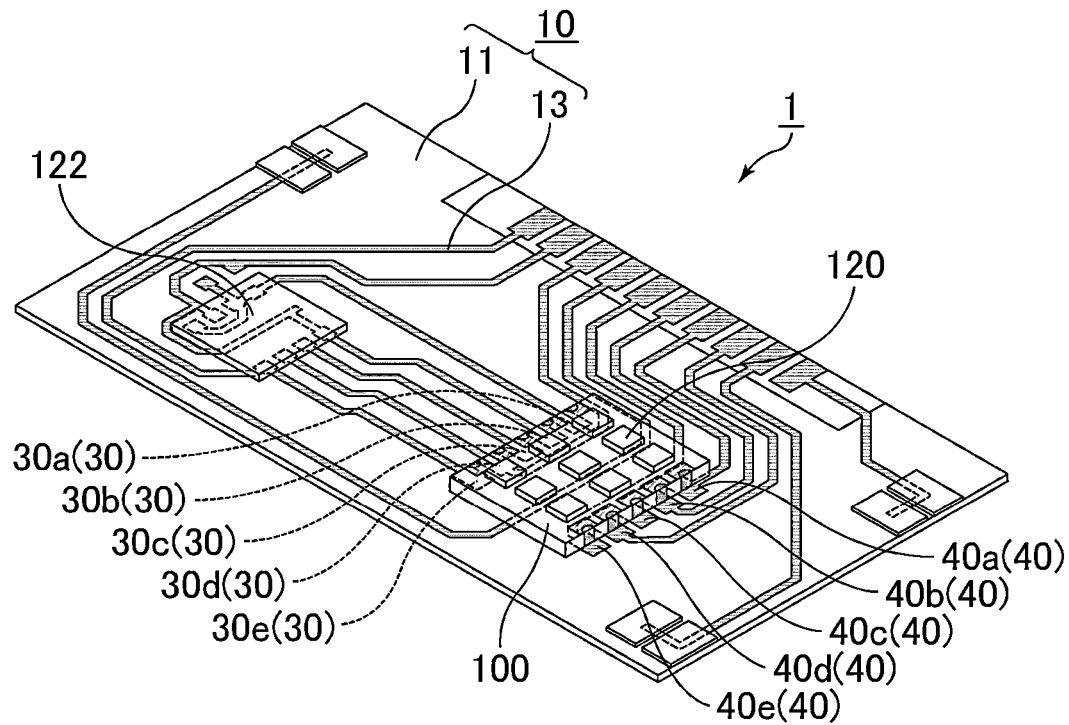

STRETCHABLE MOUNTING SUBSTRATE

CROSS REFERENCE TO RELATED APPLICATIONS

The present application is a continuation of International application No. PCT/JP2022/014498, filed Mar. 25, 2022, which claims priority to Japanese Patent Application No. 2021-093823, filed Jun. 3, 2021, the entire contents of each of which are incorporated herein by reference.

FIELD OF THE INVENTION

The present invention relates to a stretchable mounting substrate.

BACKGROUND OF THE INVENTION

In recent years, there has been a demand for a device that is brought into contact with a living body to measure biological data. Such devices include a stretchable base material and an electronic component mounted on the stretchable base material. Such a device is also referred to as a stretchable substrate, and is arranged in close contact with a living body by expansion and contraction of the stretchable base material, and can follow the operation of the living body.

In the above device, not only biological data is measured, but also irradiating an electromagnetic wave or causing a minute current to flow through the living body to heal the living body or accelerate natural recovery has been proposed.

For example, Patent Document 1 discloses that in a stretchable substrate including a base material (also referred to as a stretchable base material) made of a stretchable material and an island made of a material having a Young's modulus larger than that of the base material, the island is embedded in the base material to form an element (also referred to as an electronic component) on the island.

Patent Document 1: Japanese Patent Application Laid-Open No. 2014-162124

SUMMARY OF THE INVENTION

In the stretchable substrate as described in Patent Document 1, it is necessary to mount a corresponding electronic component on the stretchable substrate in order to acquire biological data. Therefore, it is required to mount as many electronic components as possible in order to acquire various biological data.

However, in the stretchable substrate as in Patent Document 1, there is a problem that flexibility is lost as the number of electronic components to be mounted increases.

In addition, as the number of electronic components to be mounted on the stretchable base material increases, the circuit becomes more complicated. When the circuit becomes complicated, the area of the stretchable substrate necessary for routing the stretchable wiring increases, so that the cost for the stretchable base material increases. However, there is a case where the stretchable base material that is in direct contact with a living body is disposable in consideration of hygiene, and thus it is required to suppress manufacturing cost.

Furthermore, since the stretchable wirings are routed around the electronic component, it is likely that the stretchable wirings intersect each other. At a portion where the stretchable wirings intersect each other, it is necessary to provide an insulating layer for insulation between the stretchable wirings overlapping in the vertical direction, and there is a problem that flexibility of the stretchable wiring substrate is thereby reduced.

In addition, the stretchable wiring has lower conductivity than ordinary metal wiring. Therefore, in order to suppress an increase in wiring resistance of the entire stretchable wiring substrate, it is required that the wiring length of the stretchable wiring is as short as possible.

FIG. 1 is a top view schematically illustrating an example of a conventional stretchable mounting substrate.

A stretchable mounting substrate 501 illustrated in FIG. 1 includes a stretchable base material 511, stretchable wirings 513 provided on the stretchable base material 511, and ten electronic components 520 directly mounted on the stretchable base material 511.

In the stretchable mounting substrate 501 illustrated in FIG. 1, cross wiring in which some of stretchable wirings connecting the electronic components 520 intersect is generated in regions indicated by broken lines X and Y. Therefore, there is a problem that the stretchability of the stretchable mounting substrate 501 is reduced.

Furthermore, the wiring length increases due to the routing of the stretchable wiring, and an increase in wiring resistance also becomes a problem.

The present invention has been made to solve the above problems, and an object of the present invention is to provide a stretchable mounting substrate capable of achieving both improvement in mounting density of electronic components and reduction in manufacturing cost while maintaining flexibility of the entire stretchable mounting substrate.

A stretchable mounting substrate of the present invention includes: a stretchable wiring substrate, wherein the stretchable wiring substrate includes a stretchable base material and a stretchable wiring arranged on the stretchable base material; and a module on a surface of the stretchable wiring substrate, wherein the module includes a multilayer substrate, a plurality of electronic components on a principal surface of the multilayer substrate, a plurality of first electrodes and a plurality of second electrodes on the principal surface of the multilayer substrate and electrically connected to the stretchable wiring substrate, and internal wirings inside the multilayer substrate, wherein the module has a first electrode arrangement region where the plurality of first electrodes are arranged and a second electrode arrangement region where the plurality of second electrodes are arranged, wherein an internal wiring of the internal wirings electrically connects a first electrode of the plurality of first electrodes and a second electrode of the plurality of second electrodes to form a node electrode pair, and wherein the internal wiring of the node electrode pair and the stretchable wiring on the stretchable base material intersect each other in plan view of the stretchable wiring substrate.

According to the present invention, it is possible to provide a stretchable mounting substrate capable of achieving both improvement in mounting density of electronic components and reduction in manufacturing cost while maintaining flexibility of the entire stretchable mounting substrate.

BRIEF EXPLANATION OF THE DRAWINGS

FIG. 1 is a top view schematically illustrating an example of a conventional stretchable mounting substrate.

FIG. 2 is a perspective view schematically illustrating an example of a stretchable mounting substrate of the present invention.

DETAILED DESCRIPTION OF THE INVENTION

Figure 3:
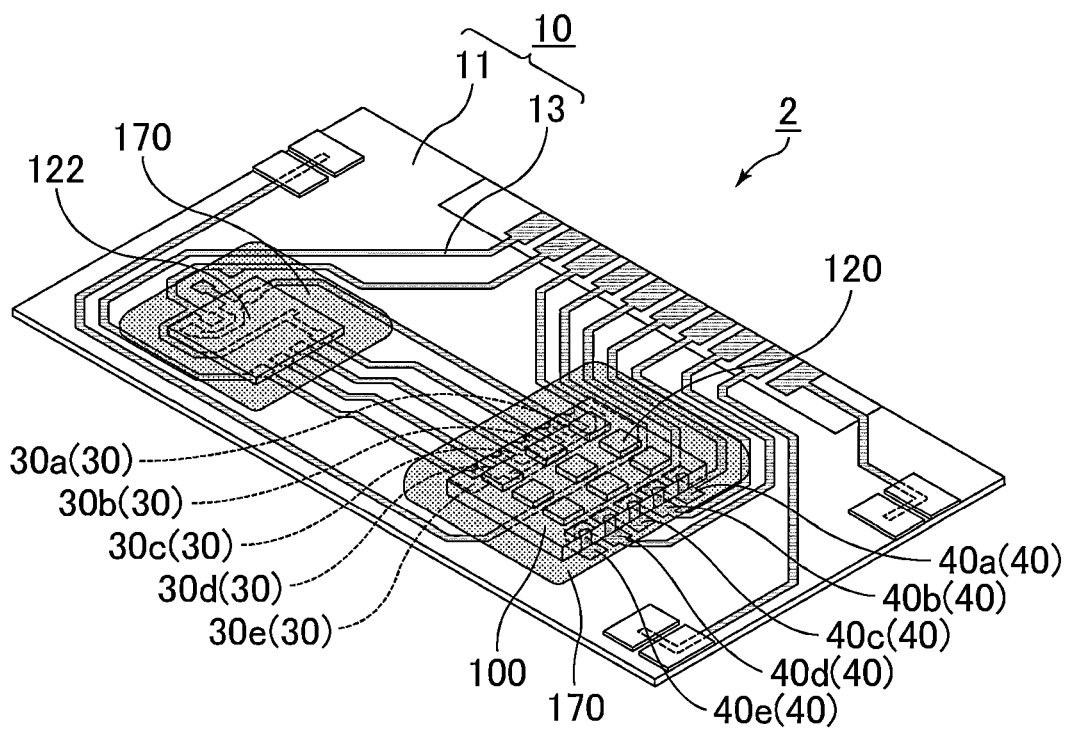
FIG. 3 is a perspective view schematically illustrating another example of the stretchable mounting substrate of the present invention.

Hereinafter, a stretchable mounting substrate of the present invention will be described. The present invention is not limited to the following configurations, and may be modified as appropriate without departing from the gist of the present invention. Further, a combination of a plurality of individual preferable configurations described below is also the present invention.

FIG. 2 is a perspective view schematically illustrating an example of a stretchable mounting substrate of the present invention.

As illustrated in FIG. 2, a stretchable mounting substrate 1 includes a stretchable wiring substrate 10 and a module 100.

The stretchable wiring substrate 10 includes a stretchable base material 11 and stretchable wirings 13 arranged on the stretchable base material 11.

The stretchable base material 11 is made of, for example, a stretchable resin material. Examples of the resin material include thermoplastic polyurethane.

The thickness of the stretchable base material 11 is not particularly limited, but is preferably 100 μm or less, and more preferably 1 μm or less, from the viewpoint of not hindering the expansion and contraction of the surface of the living body when the stretchable base material 11 is attached to the living body. In addition, the thickness of the stretchable base material 11 is preferably 0.1 μm or more.

The stretchable wiring 13 preferably contains conductive particles and a resin. Examples thereof include a mixture of metal powders such as Ag, Cu, and Ni as conductive particles and an elastomer-based resin such as a silicone resin.

The average particle size of the conductive particles is not particularly limited, but is preferably 0.01 μm to 10 μm.

The thickness of the stretchable wiring 13 is not particularly limited, but is preferably 100 μm or less, and more preferably 50 μm or less. In addition, the thickness of the stretchable wiring is preferably 0.01 μm or more.

The line width of the stretchable wiring 13 is not particularly limited, but is preferably 0.1 μm to 10 mm. Note that the minimum line width of the stretchable wiring 13 refers to a line width of a portion having the shortest line width in the stretchable wiring 13 arranged on the stretchable base material 11.

In the stretchable mounting substrate of the present invention, it is preferable that the stretchable wirings do not intersect each other on the stretchable base material. For example, in the stretchable mounting substrate 1 illustrated in FIG. 2, the stretchable wirings 13 do not intersect each other on the stretchable base material 11.

In the stretchable mounting substrate, the circuit becomes more complicated as the number of electronic components mounted on the stretchable base material increases. When the circuit becomes complicated, it is likely to be necessary to form a cross wiring in which stretchable wirings intersect each other on a stretchable base material. However, when the cross wiring is formed, there occurs a problem that the flexibility of the stretchable mounting substrate in the region where the cross wiring is formed is reduced.

Further, in order to form the cross wiring, it is necessary to add a manufacturing process. For example, a process of providing an insulating layer on the stretchable wiring serving as the lower layer and further providing the stretchable wiring thereon is required. Such complication of the manufacturing process leads to an increase in manufacturing cost, which is not preferable.

For example, in a stretchable mounting substrate 501 illustrated in FIG. 1, a total of three cross wirings are generated in a region indicated by X and a region indicated by Y. Therefore, when the stretchable mounting substrate 501 is manufactured, after a process of forming stretchable wirings 513 on a stretchable base material 511 is provided, a process of forming an insulating layer and a process of forming a stretchable wiring to be an upper layer are further required.

When the stretchable wirings do not intersect each other on the stretchable base material, a manufacturing process for providing the cross wiring on the stretchable mounting substrate is not required, and the manufacturing cost can be reduced. In addition, it is possible to suppress the decrease in the flexibility of the stretchable wiring substrate due to the formation of the cross wiring.

Electrodes 30 (30a, 30b, 30c, 30d, and 30e) and electrodes 40 (40a, 40b, 40c, 40d, and 40e) for electrically connecting with electronic components to be described later are provided on the surface of the stretchable wiring substrate 10.

These electrodes are connected to the stretchable wirings 13 arranged on the stretchable base material 11.

The electrode preferably contains conductive particles and a resin. As the conductive particles and the resin, those similar to the stretchable wiring 13 can be suitably used.

An electronic component may be mounted on the stretchable wiring substrate.

For example, electronic components 120 are mounted on the stretchable wiring substrate 10 illustrated in FIG. 2.

The electronic component mounted on the stretchable wiring substrate is preferably an electronic component that acquires biological data or an electronic component that emits an electromagnetic wave.

Examples of the electronic component that acquires biological data include an acceleration sensor, a temperature sensor, an oxygen saturation sensor, and a moisture sensor.

Examples of the electronic component that irradiates a living body with an electromagnetic wave include a coil component.

The electronic component mounted on the stretchable wiring substrate may be covered with a sealing resin or the like.

When the electronic component is covered with the sealing resin, it is possible to prevent deterioration of the characteristics of the electronic component due to the influence of moisture on the electronic component.

FIG. 3 is a perspective view schematically illustrating another example of the stretchable mounting substrate of the present invention.

The stretchable mounting substrate 2 illustrated in FIG. 3 is the same as the stretchable mounting substrate 1 illustrated in FIG. 2 except that electronic components and modules mounted on the stretchable wiring substrate 10 are sealed with sealing resins 170.

In the stretchable mounting substrate 2 illustrated in FIG. 3, an electronic component 122 mounted on the stretchable wiring substrate 10 is sealed with a sealing resin 170.

The module mounted on the stretchable wiring substrate may be covered with a sealing resin or the like.

When the module is covered with the sealing resin, it is possible to prevent deterioration of the characteristics of the module and the electronic component mounted on the module due to the influence of moisture.

In the stretchable mounting substrate 2 illustrated in FIG. 3, the module 100 mounted on the stretchable wiring substrate 10 is covered with the sealing resin 170.

When an electronic component mounted on a conventional stretchable wiring substrate is covered with a sealing resin, for example, the following problems occur.

The sealing resin is usually formed so as to cover a region larger than the electronic component in consideration of an error in a manufacturing process and the like. However, the sealing resin does not have flexibility unlike the stretchable base material. Therefore, there easily occurs a problem that, as the number of electronic components increases, the ratio of the resin covering the surface of the stretchable substrate increases, and the flexibility of the stretchable substrate is likely to decrease. This problem is particularly remarkable when the mounting density of the electronic component is increased to such an extent that the sealing resins covering the electronic component are in contact with each other.

That is, when an electronic component is sealed with a sealing resin, there is a problem that the higher the mounting density of the electronic component, the lower the flexibility of the stretchable substrate.

On the other hand, in the stretchable wiring substrate of the present invention, since the number of electronic components directly mounted on the stretchable wiring substrate can be reduced by using the module, by covering the module with the sealing resin, it is possible to both improve the mounting density of the electronic components and suppress the decrease in the flexibility of the stretchable wiring substrate while protecting the electronic components from the influence of moisture.

Examples of the sealing resin include an epoxy resin, an acrylic resin, and a silicone resin.

The stretchable mounting substrate of the present invention preferably has a flat portion.

For example, in the stretchable mounting substrate 1 illustrated in FIG. 2, the upper surface of the electronic component 122 is flat. Therefore, it can be said that the stretchable mounting substrate 1 has a flat portion. When the stretchable mounting substrate has the flat portion, the flat portion can be used as suction portion when a mounting machine or the like is used in handling the stretchable mounting substrate.

Note that, also when an electronic component or a module mounted on the stretchable wiring substrate is covered with the sealing resin, if the upper surface of the sealing resin is flat, the electronic component or the module becomes a flat portion that can be used as a suction portion when a mounting machine or the like is used.

For example, in the stretchable mounting substrate 2 illustrated in FIG. 3, the upper surface of the sealing resin 170 for sealing the module 100 and the upper surface of the sealing resin 170 for sealing the electronic component 122 are flat. Therefore, it can be said that the stretchable mounting substrate 2 has a flat portion.

Figure 4:
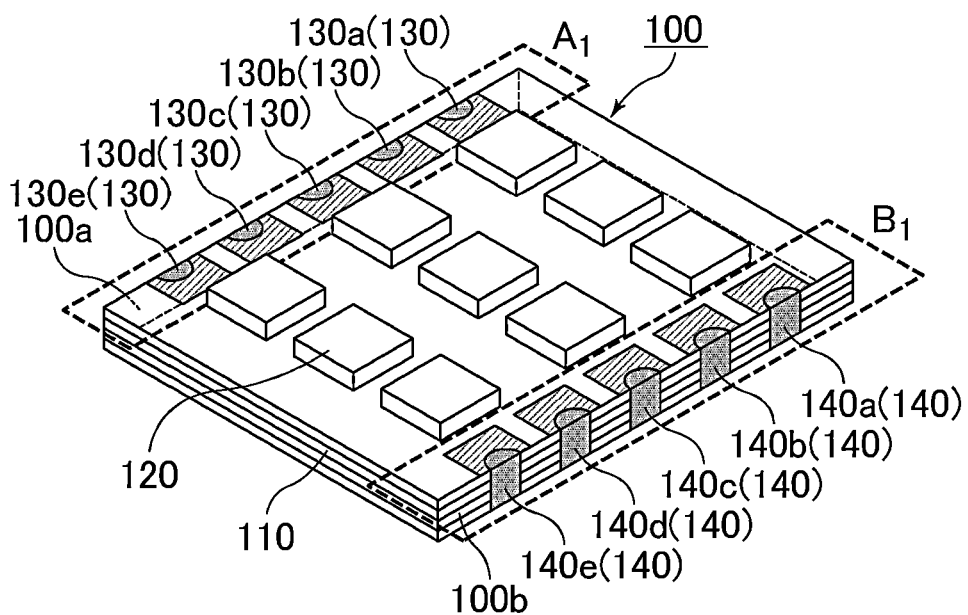
FIG. 4 is a perspective view of a module illustrated in FIGS. 2 and 3.

FIG. 4 is a perspective view of the module illustrated in FIGS. 2 and 3.

The module 100 illustrated in FIG. 4 includes a multilayer substrate 110, a plurality of electronic components 120 mounted on a principal surface of the multilayer substrate 110, a plurality of first electrodes 130 (130a, 130b, 130c, 130d, and 130e) and second electrodes 140 (140a, 140b, 140c, 140d, and 140e) provided on the principal surface of the multilayer substrate 110, and internal wirings that electrically connects the first electrodes and the second electrodes inside the multilayer substrate.

In the module 100 illustrated in FIG. 4, the number of electronic components 120 mounted on the principal surface of the multilayer substrate 110 is nine.

A region (in FIG. 4, a region $A_1$ indicated by a broken line) where the plurality of first electrodes 130 (130a, 130b, 130c, 130d, and 130e) are arranged in a concentrated manner is a first electrode arrangement region $A_1$.

A region (in FIG. 4, a region $B_1$ indicated by a broken line) where the plurality of second electrodes 140 (140a, 140b, 140c, 140d, and 140e) are arranged in a concentrated manner is a second electrode arrangement region $B_1$.

Among the first electrodes arranged in the first electrode arrangement region $A_1$ and the second electrodes arranged in the second electrode arrangement region $B_1$, two electrodes connected by an internal wiring are electrodes constituting a node electrode pair. The node electrode pair will be described later.

The first electrode arrangement region $A_1$ is located on one side 100a in plan view of the module, and the second electrode arrangement region $B_1$ is located on a side 100b opposite to the side 100a on which the first electrode arrangement region $A_1$ is arranged. When the first electrode arrangement region $A_1$ and the second electrode arrangement region $B_1$ are located on opposite sides of the module, the shortest distance between the electrode arranged in the first electrode arrangement region $A_1$ and the electrode arranged in the second electrode arrangement region $B_1$ can be increased.

Therefore, in the stretchable mounting substrate of the present invention, it is preferable that the first electrode arrangement region is located on one side in plan view of the module, and the second electrode arrangement region is located on a side opposite to the side on which the first electrode arrangement region is arranged.

A plurality of electronic components are mounted on the module.

Examples of the electronic component mounted on the multilayer substrate include an amplifier (operational amplifier, transistor, and the like), a chip capacitor, and a chip resistor. The form for mounting the electronic component is not particularly limited, and the electronic component may be mounted as a bare chip, a ball grid array (BGA), a chip-scale package (CSP), a surface mount component (SMD), or the like.

Since the stretchable mounting substrate of the present invention includes the module on which a plurality of electronic components are mounted, the number of electronic components directly mounted on the stretchable wiring substrate can be reduced.

The multilayer substrate constituting the module is formed by laminating a plurality of insulating layers.

The number of laminated insulating layers in the multilayer substrate is not particularly limited, but is preferably four or more.

In the stretchable mounting substrate of the present invention, the number of laminated insulating layers in the multilayer substrate constituting the module is preferably larger than the number of laminated stretchable base materials constituting the stretchable wiring substrate.

Examples of the material constituting the insulating layer include resins such as a phenol resin, an epoxy resin, a polyimide resin, a bismaleimide triazine resin, a fluororesin, and a polyphenylene oxide resin, and low-temperature sintering ceramic materials.

A base material made of paper or glass fiber may be impregnated with the resin constituting the insulating layer.

The low-temperature sintering ceramic material means a material that can be sintered at a firing temperature of 1000° C. or lower among ceramic materials, and can be fired simultaneously with silver or copper, which is preferably used as a metal material for an internal wiring.

The low-temperature sintering ceramic material preferably includes a $SiO_2$—CaO—$Al_2O_3$—$B_2O_3$-based glass ceramic or a $SiO_2$—MgO—$Al_2O_3$—$B_2O_3$-based glass ceramic.

The multilayer substrate includes the internal wirings.

The internal wirings electrically connect a plurality of electrodes provided on the principal surface of the multilayer substrate inside the multilayer substrate.

The internal wiring may connect the first electrode and the second electrode provided on the multilayer substrate, may connect the first electrode or the second electrode provided on the multilayer substrate and an electronic component mounted on the multilayer substrate, or may connect a plurality of electronic components mounted on the multilayer substrate.

Examples of the material constituting the internal wiring include copper, silver, tin, nickel, gold, and alloys thereof.

An example of the internal wiring provided inside the module will be described with reference to FIG. 5.

Figure 5:
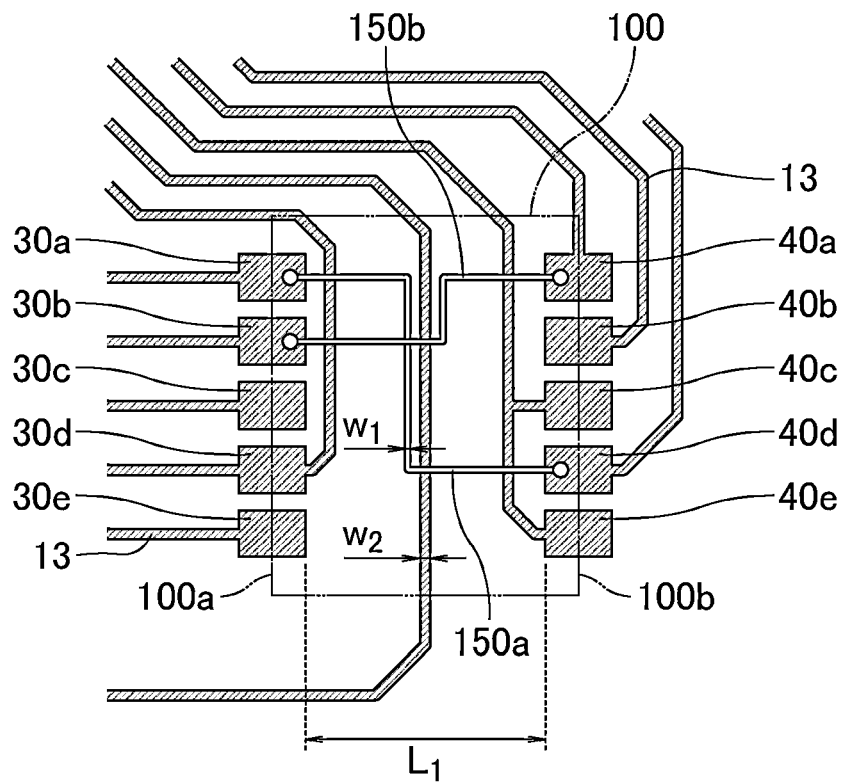
FIG. 5 is an enlarged transparent top view of a region where the module of the stretchable mounting substrate illustrated in FIGS. 2 and 3 is mounted.

FIG. 5 is an enlarged transparent top view of a region where the module of the stretchable mounting substrate illustrated in FIGS. 2 and 3 is mounted.

In FIG. 5, the module illustrated in FIG. 4 is mounted on a stretchable wiring substrate provided with the electrodes 30 (30a, 30b, 30c, 30d, and 30e) and the electrodes 40 (40a, 40b, 40c, 40d, and 40e).

In FIG. 5, a rectangular shape indicated by a two-dot chain line indicates the position of the module 100 mounted on the stretchable wiring substrate 10.

In FIG. 5, the first electrodes 130 (130a, 130b, 130c, 130d, and 130e) and the second electrodes 140 (140a, 140b, 140c, 140d, and 140e) of the module 100 illustrated in FIG. 4 are arranged so as to overlap the electrodes 30 (30a, 30b, 30c, 30d, and 30e) and the electrodes 40 (40a, 40b, 40c, 40d, and 40e) provided on the stretchable wiring substrate, respectively, in plan view. Therefore, it can be said that the module 100 and the stretchable wiring substrate are electrically connected via electrodes.

As illustrated in FIG. 5, the module 100 includes internal wiring 150a and internal wiring 150b.

In the stretchable mounting substrate of the present invention, it can be said that a part of the stretchable wiring originally arranged on the stretchable base material is mounted as the internal wiring in the module. The necessary area of the stretchable base material can be reduced by replacing a part of the stretchable wiring arranged on the stretchable base material with the internal wiring arranged in the module. Therefore, by reducing the area of the stretchable base material, it is possible to reduce the size and cost of the stretchable mounting substrate.

The internal wiring 150a electrically connects the first electrode 130a and the second electrode 140d. The first electrode 130a and the second electrode 140d connected by the internal wiring 150a have the same potential.

The internal wiring 150b electrically connects the first electrode 130b and the second electrode 140a. The first electrode 130b and the second electrode 140a connected by the internal wiring 150b have the same potential.

In the present specification, a pair of the two first electrode and second electrode having the same potential through the internal wiring are also referred to as a node electrode pair. That is, the first electrode 130a and the second electrode 140d are a node electrode pair, and the first electrode 130b and the second electrode 140a are a node electrode pair.

As illustrated in FIG. 5, the module 100 has two sets of node electrode pairs.

The two electrodes (the first electrode 130a and the second electrode 140d, and the first electrode 130b and the second electrode 140a) constituting the node electrode pair are provided separately in the first electrode arrangement region $A_1$ and the second electrode arrangement region $B_1$. In other words, the two electrodes constituting the node electrode pair are not arranged in the same electrode arrangement region.

In the stretchable mounting substrate of the present invention, the internal wiring constituting the node electrode pair and the stretchable wiring arranged on the stretchable base material intersect each other in plan view of the stretchable mounting substrate.

For example, in the stretchable mounting substrate 1 illustrated in FIG. 5, the internal wiring 150a and the internal wiring 150b intersect the stretchable wiring 13 connected to the electrode 30d and the stretchable wiring 13 connected to the electrodes 40c and 40e, respectively.

It can be said that the above-described configuration of the internal wirings is an example in which stretchable wirings intersect each other in a case where stretchable wirings are used instead of the internal wirings formed in the module. Therefore, it can be said that the stretchable mounting substrate of the present invention has a configuration capable of avoiding the arrangement of the stretchable wirings in which the cross wiring is formed on the stretchable base material. Therefore, it is possible to suppress a decrease in flexibility of the stretchable mounting substrate and an increase in manufacturing cost due to the formation of the cross wiring.

In the stretchable mounting substrate of the present invention, when the module is viewed in plan view, it is preferable that the internal wirings constituting the pair of node electrodes intersect each other in the multilayer substrate in plan view.

For example, in FIG. 5, the internal wiring 150a constituting the node electrode pair and the internal wiring 150b constituting another node electrode pair intersect each other in plan view of the module 100.

The internal wiring 150a and the internal wiring 150b are located in different layers of the multilayer substrate. Therefore, if the internal wiring 150a and the internal wiring 150b intersect each other in plan view, the internal wiring 150a and the internal wiring 150b are not in electrical contact with each other.

The line widths (length indicated by double-headed arrow $w_1$ in FIG. 5) of the internal wiring 150a and the internal wiring 150b provided in the module 100 are shorter than the minimum line width (length indicated by double-headed arrow $w_2$ in FIG. 5) of the stretchable wiring 13.

That is, in the stretchable mounting substrate of the present invention, the minimum line width of the internal wiring is preferably shorter than the minimum line width of the stretchable wiring. When the minimum line width of the internal wiring is shorter than the minimum line width of the stretchable wiring, the wiring density of the module can be made higher than the wiring density of the stretchable substrate, which contributes to downsizing of the stretchable mounting substrate.

The minimum line width of the internal wiring is not particularly limited, but is preferably, for example, 100 μm or less.

The shortest distance between the first electrodes arranged in the first electrode arrangement region $A_1$ and the second electrodes arranged in the second electrode arrangement region $B_1$ is a length indicated by a double-headed arrow $L_1$. The length $L_1$ is preferably longer than the minimum line width $w_2$ of the stretchable wiring 13 arranged on the stretchable base material 11.

That is, the shortest distance between the first electrode and the second electrode constituting the node electrode pair is preferably longer than the minimum line width of the stretchable wiring.

When the length $L_1$ is longer than the length $w_2$, it can be said that a gap through which the stretchable wiring 13 can pass exists between the first electrode arranged in the first electrode arrangement region $A_1$ and the second electrode arranged in the second electrode arrangement region $B_1$. Therefore, it is possible to provide the stretchable wiring 13 that crosses the module 100 in plan view between the stretchable wiring substrate 10 and the module 100.

The minimum interval of the stretchable wirings is a minimum interval at which a pattern can be formed while avoiding interference when two stretchable wirings are arranged in parallel. The minimum interval of the stretchable wirings is appropriately determined by a material constituting the stretchable wiring, a material constituting the stretchable base material, a voltage of a power supply connected to the stretchable mounting substrate, and the like.

The minimum interval of the stretchable wirings is, for example, preferably 300 μm or less, and more preferably 200 μm or less.

The length $L_1$ is preferably larger than the sum of the minimum line width of the stretchable wiring and the value twice the minimum interval of the stretchable wirings.

When the length $L_1$ is larger than the sum of the minimum line width of the stretchable wiring and the value twice the minimum interval of the stretchable wirings, a pattern in which one stretchable wiring having a minimum line width passing through a point bisecting the length $L_1$ between the electrodes is arranged so as not to interfere with the electrodes can be formed between the stretchable wiring substrate and the module.

That is, in the stretchable mounting substrate of the present invention, the shortest distance between the first electrode and the second electrode constituting the node electrode pair is preferably larger than the sum of the minimum line width of the stretchable wiring and the value twice the minimum interval of the stretchable wirings.

The length $L_1$ is preferably larger than the sum of the value twice the minimum line width of the stretchable wiring and a value three times the minimum interval of the stretchable wirings.

When the length $L_1$ is larger than the sum of the value twice the minimum line width of the stretchable wiring and the value three times the minimum interval of the stretchable wirings, a pattern in which two stretchable wirings each having a minimum line width passing through two points that divide the length $L_1$ between the electrodes into three equal parts are arranged so as not to interfere with an adjacent electrode and an adjacent stretchable wiring can be formed between the stretchable wiring substrate and the module.

The length $L_1$ is preferably larger than the sum of the value three times the minimum line width of the stretchable wiring and a value four times the minimum interval of the stretchable wirings.

When the length $L_1$ is larger than the sum of the value three times the minimum line width of the stretchable wiring and the value four times the minimum interval of the stretchable wirings, a pattern in which three stretchable wirings each having a minimum line width passing through three points that divide the length $L_1$ between the electrodes into four equal parts are arranged so as not to interfere with an adjacent electrode and/or an adjacent stretchable wiring can be formed between the stretchable wiring substrate and the module.

In the module 100 illustrated in FIGS. 2, 3, 4, and 5, all the electrodes (the first electrodes 130 and the second electrodes 140) are arranged on the side 100a and the side 100b of the module 100, but in the stretchable mounting substrate of the present invention, the electrodes may be arranged at positions away from the sides of the module.

An example in which electrodes are arranged at positions away from the sides of the module will be described with reference to FIG. 6.

Figure 6:
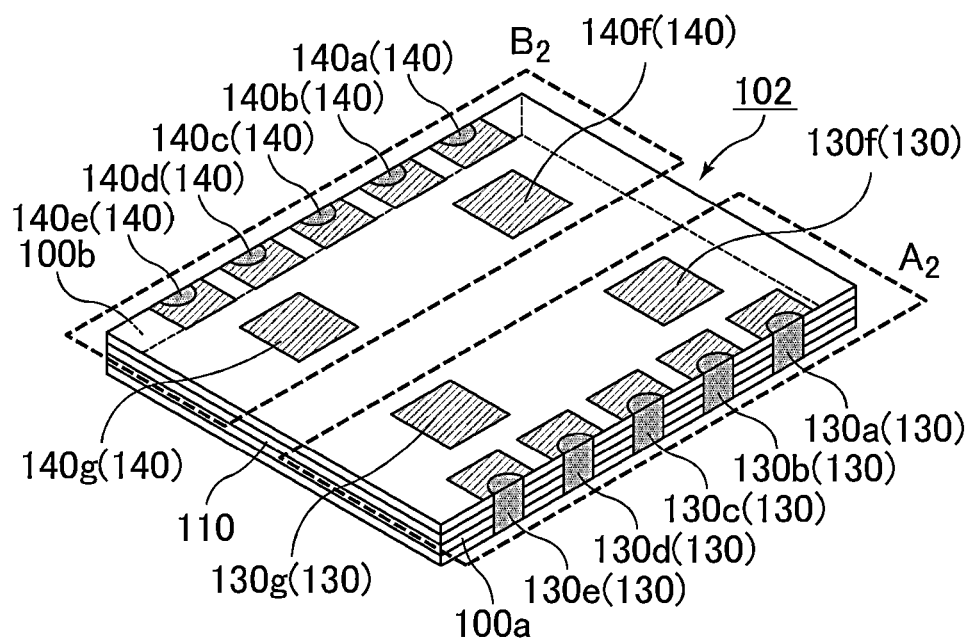
FIG. 6 is a perspective view schematically illustrating another example of the module constituting the stretchable mounting substrate of the present invention.

FIG. 6 is a perspective view schematically illustrating another example of the module constituting the stretchable mounting substrate of the present invention.

A module 102 illustrated in FIG. 6 corresponds to the module 100 illustrated in FIG. 4 in which electrodes 130f, 130g, 140f, and 140g are further provided on a principal surface on which no electronic component is mounted. That is, the module 102 illustrated in FIG. 6 is reversed in front and back from the module 100 illustrated in FIG. 4.

Each of the electrode 130f, the electrode 130g, the electrode 140f, and the electrode 140g is an electrode provided at a position away from the side of the module.

Here, when it is determined which of the first electrode arrangement region and the second electrode arrangement region the electrode provided in the module belongs to, if the electrode constitutes a node electrode pair, the electrode belongs to an electrode arrangement region different from the electrode arrangement region where an electrode to be a pair connected by the internal wiring is arranged. On the other hand, when the electrode provided in the module is not an electrode constituting a node electrode pair, the electrode belongs to an electrode arrangement region where an electrode arranged at the closest position in plan view is arranged.

First, similarly to the module 100 illustrated in FIG. 4, the electrodes 130a, 130b, 130c, 130d, and 130e belong to a first electrode arrangement region $A_2$. The electrodes 140a, 140b, 140c, 140d, and 140e belong to a second electrode arrangement region $B_2$. That is, the electrodes 130a, 130b, 130c, 130d, and 130e are first electrodes, and the electrodes 140a, 140b, 140c, 140d, and 140e are second electrodes.

The electrode arranged at the position closest to the electrode 130f in plan view is the first electrode 130b. Since the first electrode 130b is an electrode belonging to the first electrode arrangement region $A_2$, the electrode 130f also belongs to the first electrode arrangement region $A_2$. That is, the electrode 130f is a first electrode.

The electrode arranged at the position closest to the electrode 130g in plan view is the first electrode 130d. Since the first electrode 130d is an electrode belonging to the first electrode arrangement region $A_2$, the electrode 130g also belongs to the first electrode arrangement region $A_2$. That is, the electrode 130g is a first electrode.

The electrode arranged at the position closest to the electrode 140f in plan view is the second electrode 140b. Since the second electrode 140b is an electrode belonging to the second electrode arrangement region $B_2$, the electrode 140f also belongs to the second electrode arrangement region $B_2$. That is, the electrode 140f is a second electrode.

The electrode arranged at the position closest to the electrode 140g in plan view is the second electrode 140d. Since the second electrode 140d is an electrode belonging to the second electrode arrangement region $B_2$, the electrode 140g also belongs to the second electrode arrangement region $B_2$. That is, the electrode 140g is a second electrode.

Therefore, in the module 102 illustrated in FIG. 6, seven first electrodes (first electrodes 130a, 130b, 130c, 130d, 130e, 130f, and 130g) are arranged in the first electrode arrangement region $A_2$. In addition, seven second electrodes (second electrodes 140a, 140b, 140c, 140d, 140e, 140f, and 140g) are arranged in the second electrode arrangement region $B_2$.

Figure 7:
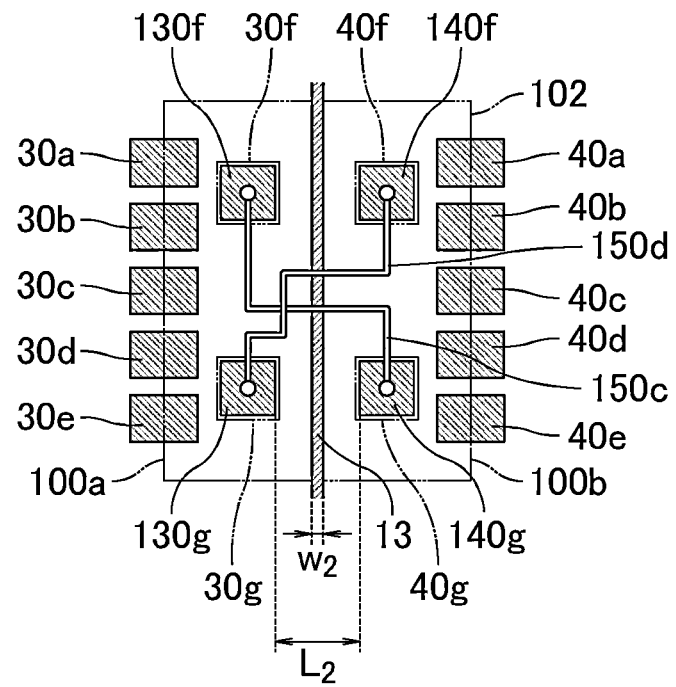
FIG. 7 is a transparent top view schematically illustrating an example of a state in which the module illustrated in FIG. 6 is mounted on a stretchable wiring substrate.

FIG. 7 is a transparent top view schematically illustrating an example of a state in which the module illustrated in FIG. 6 is mounted on a stretchable wiring substrate. In FIG. 7, among the stretchable wirings provided on the stretchable mounting substrate, only stretchable wirings that are not electrically connected to the electrodes constituting the module are illustrated, and other stretchable wirings are omitted.

In FIG. 7, the module illustrated in FIG. 6 is mounted on a stretchable wiring substrate provided with electrodes 30 (30a, 30b, 30c, 30d, 30e, 30f, and 30g) and electrodes 40 (40a, 40b, 40c, 40d, 40e, 40f, and 40g).

In FIG. 7, a rectangular shape indicated by a two-dot chain line indicates the position of the module 102 mounted on the stretchable wiring substrate.

In FIG. 7, the first electrodes 130 (130a, 130b, 130c, 130d, 130e, 130f, and 130g) and the second electrodes 140 (140a, 140b, 140c, 140d, 140e, 140f, and 140g) of the module 102 illustrated in FIG. 6 are arranged so as to overlap the electrodes 30 (30a, 30b, 30c, 30d, 30e, 30f, and 30g) and the electrodes 40 (40a, 40b, 40c, 40d, 40e, 40f, and 40g) provided on the stretchable wiring substrate, respectively, in plan view. Therefore, it can be said that the module 102 and the stretchable mounting substrate are electrically connected via electrodes.

As illustrated in FIG. 7, the multilayer substrate constituting the module 102 includes internal wirings 150c and 150d.

The internal wiring 150c electrically connects the first electrode 130f and the second electrode 140g. The first electrode 130f and the second electrode 140g connected by the internal wiring 150c have the same potential.

The internal wiring 150d electrically connects the first electrode 130g and the second electrode 140f. The first electrode 130g and the second electrode 140f connected by the internal wiring 150d have the same potential.

Therefore, the first electrode 130f and the second electrode 140g are a node electrode pair, and the first electrode 130g and the second electrode 140f are a node electrode pair.

As illustrated in FIG. 7, the module 102 has two sets of node electrode pairs.

FIG. 7 illustrates the stretchable wiring 13 crossing the module 102 in the longitudinal direction of the drawing. The shortest distance (length indicated by double-headed arrow L2 in FIG. 7) between the first electrode arranged in the first electrode arrangement region $A_2$ and the second electrode arranged in the second electrode arrangement region $B_2$ is longer than the minimum line width $w_2$ of the stretchable wiring 13. Therefore, it is possible to provide the stretchable wiring 13 that crosses the module 102 in plan view between the stretchable wiring substrate 10 and the module 102.

The module used for the stretchable mounting substrate of the present invention may be a double-sided mounting module in which electronic components are mounted on both principal surfaces of a multilayer substrate. When the module is a double-sided mounting module, the number of electronic components and wirings that can be mounted in the same area can be increased, so that the module can be downsized.

Figure 8:
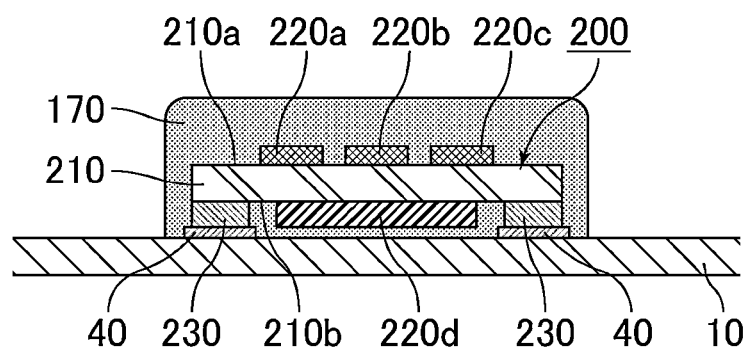
FIG. 8 is a sectional view schematically illustrating an example of a double-sided mounting module.

FIG. 8 is a sectional view schematically illustrating an example of the double-sided mounting module.

In a double-sided mounting module 200 illustrated in FIG. 8, an electronic component 220a, an electronic component 220b, and an electronic component 220c are mounted on one principal surface 210a of a multilayer substrate 210, and an electronic component 220d is mounted on the other principal surface 210b that is a principal surface opposite to the one principal surface 210a. The other principal surface 210b is provided with terminals 230 in addition to the electronic component 220d, and the terminals 230 are electrically connected to the electrodes 40 on the stretchable wiring substrate 10 to be mounted on the stretchable wiring substrate 10.

The double-sided mounting module 200 is sealed with the sealing resin 170.

The stretchable mounting substrate of the present invention can be obtained by, for example, a process of preparing a stretchable wiring substrate, a process of preparing a module, and a process of mounting the module on the stretchable wiring substrate.

DESCRIPTION OF REFERENCE SYMBOLS 1, 2: Stretchable mounting substrate
10: Stretchable wiring substrate
11: Stretchable base material
13: Stretchable wiring
30, 30a, 30b, 30c, 30d, 30e, 30f, 30g: Electrode on stretchable wiring substrate
40, 40a, 40b, 40c, 40d, 40e, 40f, 40g: Electrode on stretchable wiring substrate
100, 102: Module
100a, 100b: Side of module in plan view
110: Multilayer substrate
120, 120a, 120b, 122: Electronic component
130, 130a, 130b, 130c, 130d, 130e, 130f, 130g: First electrode
140, 140a, 140b, 140c, 140d, 140e, 140f, 140g: Second electrode
150a, 150b, 150c, 150d: Internal wiring
170: Sealing resin 200: Double-sided mounting module
210: Multilayer substrate
210a: One principal surface of multilayer substrate
210b: Other principal surface of multilayer substrate
220a, 220b, 220c, 220d: Electronic component
230: Terminal (external electrode)
501: Stretchable mounting substrate
511: Stretchable base material
513: Stretchable wiring
520: Electronic component
$A_1$, $A_2$: First electrode arrangement region
$B_1$, $B_2$: Second electrode arrangement region
$L_1$, $L_2$: Shortest distance between first electrode arranged in first electrode arrangement region and second electrode arranged in second electrode arrangement region
$w_1$: Line width of internal wiring
$w_2$: Minimum line width of stretchable wiring
X, Y: Region where cross wiring is formed

The invention claimed is:

1. A stretchable mounting substrate comprising:
a stretchable wiring substrate, wherein the stretchable wiring substrate includes a stretchable base material and a stretchable wiring arranged on the stretchable base material; and
a module on a surface of the stretchable wiring substrate, wherein the module includes a multilayer substrate, a plurality of electronic components on a principal surface of the multilayer substrate, a plurality of first electrodes and a plurality of second electrodes on the principal surface of the multilayer substrate and electrically connected to the stretchable wiring substrate, and internal wirings inside the multilayer substrate,
wherein the module has a first electrode arrangement region where the plurality of first electrodes are arranged and a second electrode arrangement region where the plurality of second electrodes are arranged,
wherein an internal wiring of the internal wirings electrically connects a first electrode of the plurality of first electrodes and a second electrode of the plurality of second electrodes to form a node electrode pair, and
wherein the internal wiring of the node electrode pair and the stretchable wiring on the stretchable base material intersect each other in plan view of the stretchable wiring substrate.

2. The stretchable mounting substrate according to claim 1, wherein a shortest distance between the first electrode and the second electrode of the node electrode pair is longer than a minimum line width of the stretchable wiring.

3. The stretchable mounting substrate according to claim 2, wherein a minimum line width of the internal wiring in the module is shorter than the minimum line width of the stretchable wiring.

4. The stretchable mounting substrate according to claim 1, wherein a shortest distance between the first electrode and the second electrode of the node electrode pair is longer than a sum of a minimum line width of the stretchable wiring and a value twice a minimum interval of the stretchable wiring.

5. The stretchable mounting substrate according to claim 4, wherein a minimum line width of the internal wiring in the module is shorter than the minimum line width of the stretchable wiring.

6. The stretchable mounting substrate according to claim 1, wherein a minimum line width of the internal wiring in the module is shorter than a minimum line width of the stretchable wiring.

7. The stretchable mounting substrate according to claim 1, wherein a number of layers in the multilayer substrate of the module is larger than a number of laminated stretchable base materials of the stretchable wiring substrate.

8. The stretchable mounting substrate according to claim 1, wherein the stretchable wiring does not intersect on the stretchable base material.

9. The stretchable mounting substrate according to claim 1, wherein the module is a double-sided mounting module in which the plurality of electronic components are mounted on opposed surfaces of the multilayer substrate.

10. The stretchable mounting substrate according to claim 1, wherein the first electrode arrangement region is located on a first side of the module in the plan view, and the second electrode arrangement region is located on a second side of the module opposite to the first side.

11. The stretchable mounting substrate according to claim 10, wherein each of the first electrode and the second electrode of the node electrode pair is positioned away from the first side and the second side, respectively, of the module.

12. The stretchable mounting substrate according to claim 1, further comprising a sealing resin sealing at least the module.

13. The stretchable mounting substrate according to claim 1, wherein at least a part of the stretchable mounting substrate has a flat portion.

* * * * *